United States Patent [19]

Carr et al.

[11] Patent Number: 5,334,141
[45] Date of Patent: Aug. 2, 1994

[54] EXTRAVASATION DETECTION SYSTEM AND APPARATUS

[75] Inventors: Kenneth L. Carr, Harvard; James F. Regan, Waltham, both of Mass.; Seid W. Waddell, Sarver, Pa.

[73] Assignee: Medrad, Inc., Pittsburgh, Pa.

[21] Appl. No.: 904,651

[22] Filed: Jun. 26, 1992

[51] Int. Cl.$^5$ .................... A61M 31/00; A61B 5/04; A61B 5/05

[52] U.S. Cl. .................... 604/50; 604/65; 604/66; 604/67; 128/639; 128/653.3; 128/DIG. 13

[58] Field of Search ............ 128/637, 639, 640, 653.1, 128/653.2, 653.3, 687, 723, 724, D12, D13; 343/718; 604/50-53, 65-67, 99-100, 118, 131-133

[56] References Cited

U.S. PATENT DOCUMENTS 4,647,281 3/1987 Carr .
4,653,501 3/1987 Cartmell et al. .................... 128/640

Primary Examiner—Randall L. Green
Assistant Examiner—P. Zuttarelli
Attorney, Agent, or Firm—Keck, Mahin & Cate

[57] ABSTRACT

A system is disclosed for detecting extravasation of injected liquid from the blood vessel of a patient. The system operates by monitoring electromagnetic microwave emission from the patient at the injection site by means of a microwave antenna assembly and processing apparatus connected to the antenna assembly for responding to changes in the microwave emission characteristics representative of extravasation. The antenna assembly has a reusable antenna element connected to the processing apparatus, a disposable attachment element for adhering to the patient's skin, and interfitting male and female coupling formations on the attachment element and the antenna element respectively for releasably coupling the reusable element to the disposable element.

22 Claims, 7 Drawing Sheets

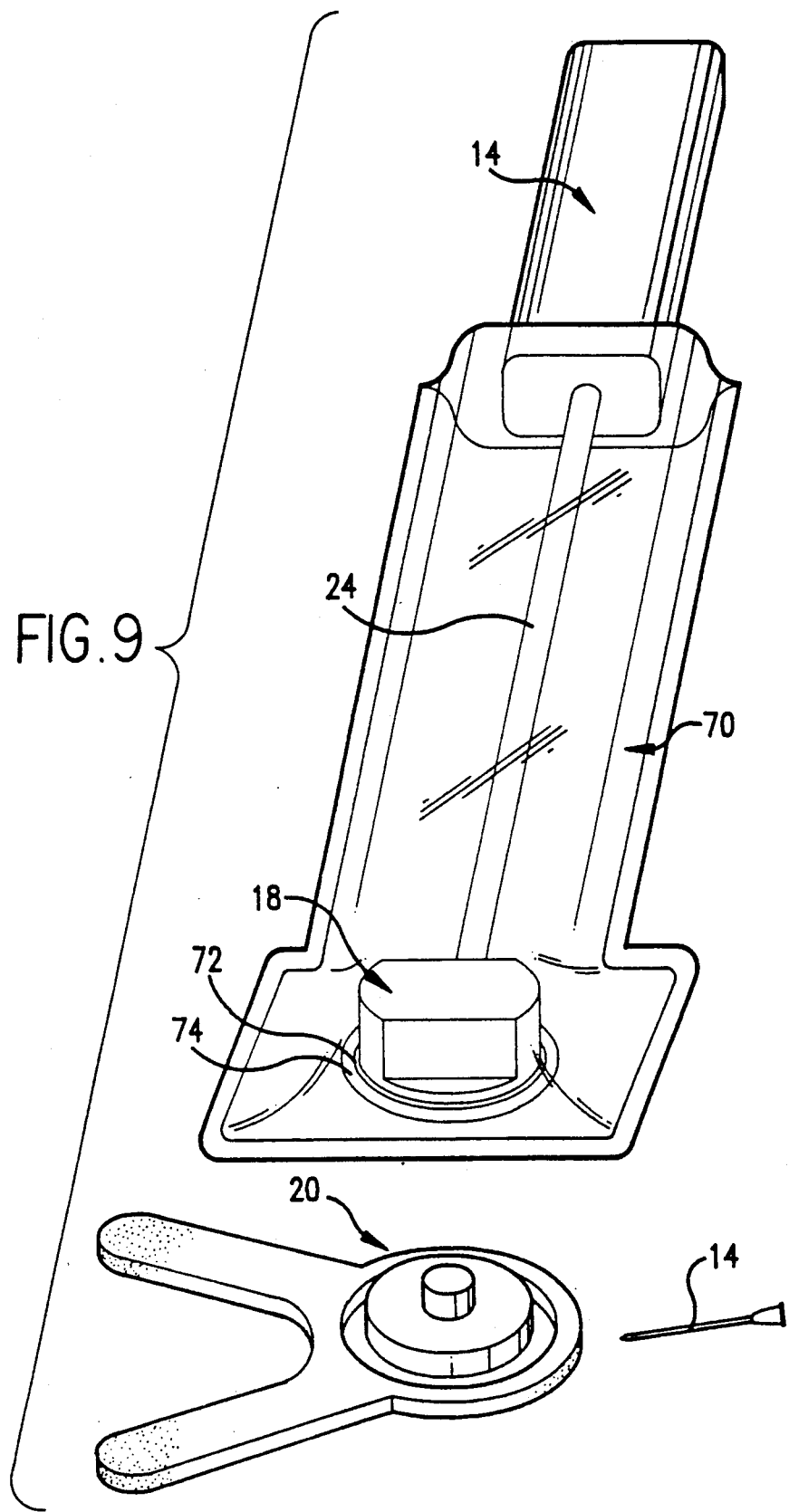

EXTRAVASATION DETECTION SYSTEM AND APPARATUS

BACKGROUND OF THE INVENTION

This invention relates to an extravasation detection system and apparatus.

Extravasation is the accidental infusion of an injection fluid such as a contrast medium, a medicinal fluid or the like into tissue surrounding a patient's blood vessel, rather than into the vessel itself. Extravasation can be caused, for example, by fragile vasculature, inappropriate needle placement, or patient movement, causing the infusing cannula to be pulled from the intended vessel or to be pushed through the wall of the vessel. Also, it is possible for the injection pressure to cause the fluid to be ejected from the vessel at the site of cannula penetration.

Certain injected fluids, such as those used for contrast enhancement or in chemotherapy can be toxic to tissue if concentrated and not diluted by blood flow through the vessel. Accordingly, it is important to detect an extravasation occurrence quickly so that injection of the fluid can be halted before a large volume of fluid has been injected into the surrounding tissue.

A number of prior art systems have been proposed for extravasation detection. One such system is disclosed in U.S. Pat. No. 4,647,281 and comprises a microwave antenna which is secured to a patient's skin over an injection site, and a microwave radiometer connected by a coaxial cable to the antenna. The system uses microwave radiation technology to detect abnormal subcutaneous temperature changes in the area of the injection site resulting from extravasation, and to generate a signal responsive to such changes. The signal is used as an alarm to halt injection of the fluid. In one embodiment of the system, two microwave antennas may be used to generate comparative signals between the injection site and an adjacent area of the patient's skin. The patent discloses disposable microwave antennas incorporated in flexible adhesive patches to be attached in conforming relation to the skin, and also indicates that more expensive reusable antennas can be used in the system.

SUMMARY OF THE INVENTION

Broadly stated, it is an object of the present invention to provide a microwave extravasation detection system of the general kind disclosed in the aforementioned U.S. patent, which employs a reusable microwave antenna element, and a disposable attachment element for releasably securing the antenna element to a patient's skin over an injection site, in such a manner as to provide intimate contact of the antenna element with the skin, optimizing microwave transfer between the skin and the antenna while shielding the antenna element from environmental noise signals.

With the above arrangement, the antenna element can be a permanent part of an infusion and detection system and the attachment element can be a relatively inexpensive item which can be disposed of after a single use. According to the invention, the attachment element may have an adhesive-backed carrier sheet or film for adherence to the skin and a coupling formation on the carrier sheet which interfits with a complimentary coupling formation on the antenna element, with a male and female connection, so that the coupling formation on the carrier sheet forms, with the antenna element, a composite microwave antenna structure. Thus, in one preferred form of the invention, the coupling formation on the carrier sheet comprises a button of dielectric material which fits intimately into a corresponding recess in dielectric material of the reusable antenna element thereby forming a substantially continuous dielectric antenna mass. Surrounding the button, the carrier sheet may include a further adhesive layer onto which a metallic housing part of the reusable element fits to secure same intimately to the skin.

Pursuant to the above object, therefore, the invention sets out, inter alia, to provide a disposable attachment element for a passive electromagnetic microwave detection antenna, which allows for intimate contact with the skin (no appreciable air gap) and which does not interfere with signal detection. The attachment element includes a mass-producible dielectric coupling material to mate with complimentary dielectric material of the antenna element and to match the electrical impedance of body tissue with that of the antenna so that transcutaneous coupling is maximized. Further, the attachment element provides a geometry for the dielectric material which minimizes leakage of spurious radiation from the environment into the antenna while providing stable orientation of the antenna centered on the tip of the infusing cannula.

Additionally, the attachment element holds the antenna firmly to the patient's skin, while allowing simple detachment and not unduly complicating the infusion procedure. The attachment element provides a sterile barrier between the antenna and the injection site to minimize patient to patient cross-contamination of blood products, while also providing open access to the skin area surrounding the antenna to allow tactile and visual monitoring before, during and after injection.

Further, the attachment element aids in accurate positioning of the antenna over the tip of the infusion cannula and preferably allows attachment of the antenna element at any rotational angle so that the antenna cable will not interfere with the infusion tubing or with the tactile and visual monitoring of the injection site.

The attachment element may also provide a sterile barrier to reduce the possibility of contamination of the reusable antenna element. The attachment should be non-toxic and should simultaneously meet the criteria of high volume manufacture and sterilization without change in its properties. The attachment element should also be designed to maximize signal change when the reusable antenna element is not properly positioned thereon and maximize the possibility that the system can detect this condition.

Additional objects and advantages of the invention will be apparent from the ensuing description and claims read in conjunction with the attached drawings.

BRIEF DESCRIPTION OF DRAWINGS

FIG. 9 is a perspective view of parts of the detection system showing a protective sterile cover for the reusable antenna element and associated cable.

DESCRIPTION OF PREFERRED EMBODIMENTS

Figure 1:
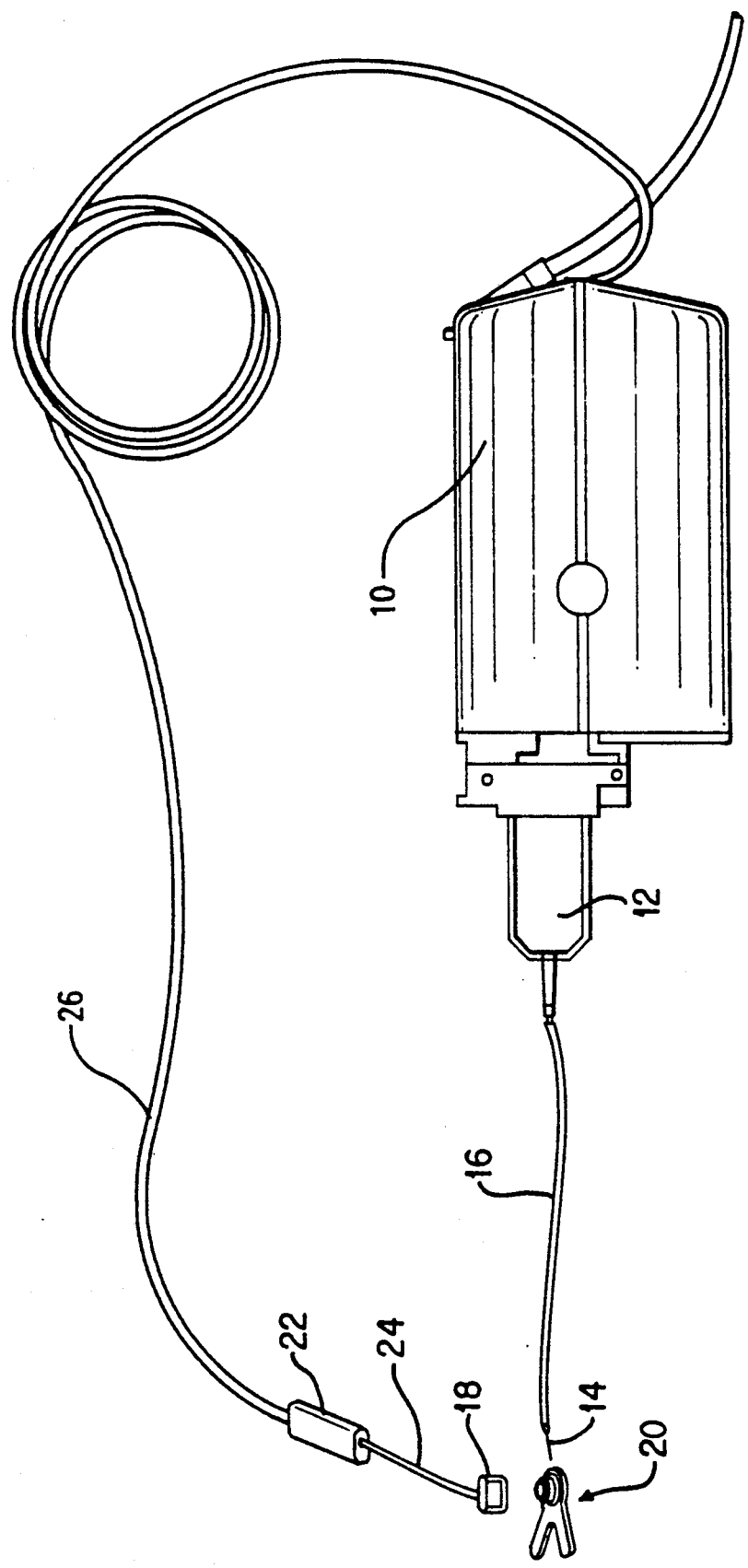
FIG. 1 is a somewhat diagrammatic overall view of intravenous infusion apparatus incorporating an extravasation detection system in accordance with the invention.

Referring initially to FIG. 1, there is illustrated an intravenous infusion apparatus comprising a known type of injector head 10 operating an infusion syringe 12 which supplies intravenous fluid, such as contrast medium, medication or the like, to a patient through an infusion cannula 14 inserted into a patient's blood vessel, and a connector tube 16. For a complete description of a type of angiographic injector, the head of which is shown at 10, reference is directed to U.S. Pat. No. 4,006,736. Associated with the infusion apparatus is a system for detecting, by microwave emission and detection, accidental extravasation of the fluid into tissue adjacent the injection site should such an event occur, and for terminating the supply of fluid responsive thereto by controlling the injector head accordingly. The detection system comprises a microwave antenna element 18 for receiving microwave signals from the patient's skin in the area of the infusion site, an attachment element 20 for releasably securing the antenna element in intimate contact to the skin over the infusion site, a radiometer 22 for amplifying signals received from the antenna element through a coaxial cable 24 and a power cable 26 connecting the radiometer to a microprocessor or the like (not shown) of the injector, a part of which is the injector head 10.

In use, changes in microwave radiation from the patient caused by extravasation of fluid into tissue adjacent the injection site are detected by the antenna and transmitted via the radiometer in the form of an electric signal to the microprocessor of the injector so that the signal can be used to terminate the supply of injected fluid. The process of microwave detection of extravasation is explained in the above-noted U.S. patent and incorporated herein by reference. The present invention is primarily concerned with the structure of the antenna part of the system for efficiently detecting changes from normal in microwave emission from the patient resulting from extravasation, and other parts of the system will not therefore be described herein in detail. The antenna part of the system, with which the present invention is primarily concerned, comprises the reusable antenna element 18 and the disposable attachment 20 for releasably securing the reusable element in intimate contact with the patient's skin.

Figure 3:
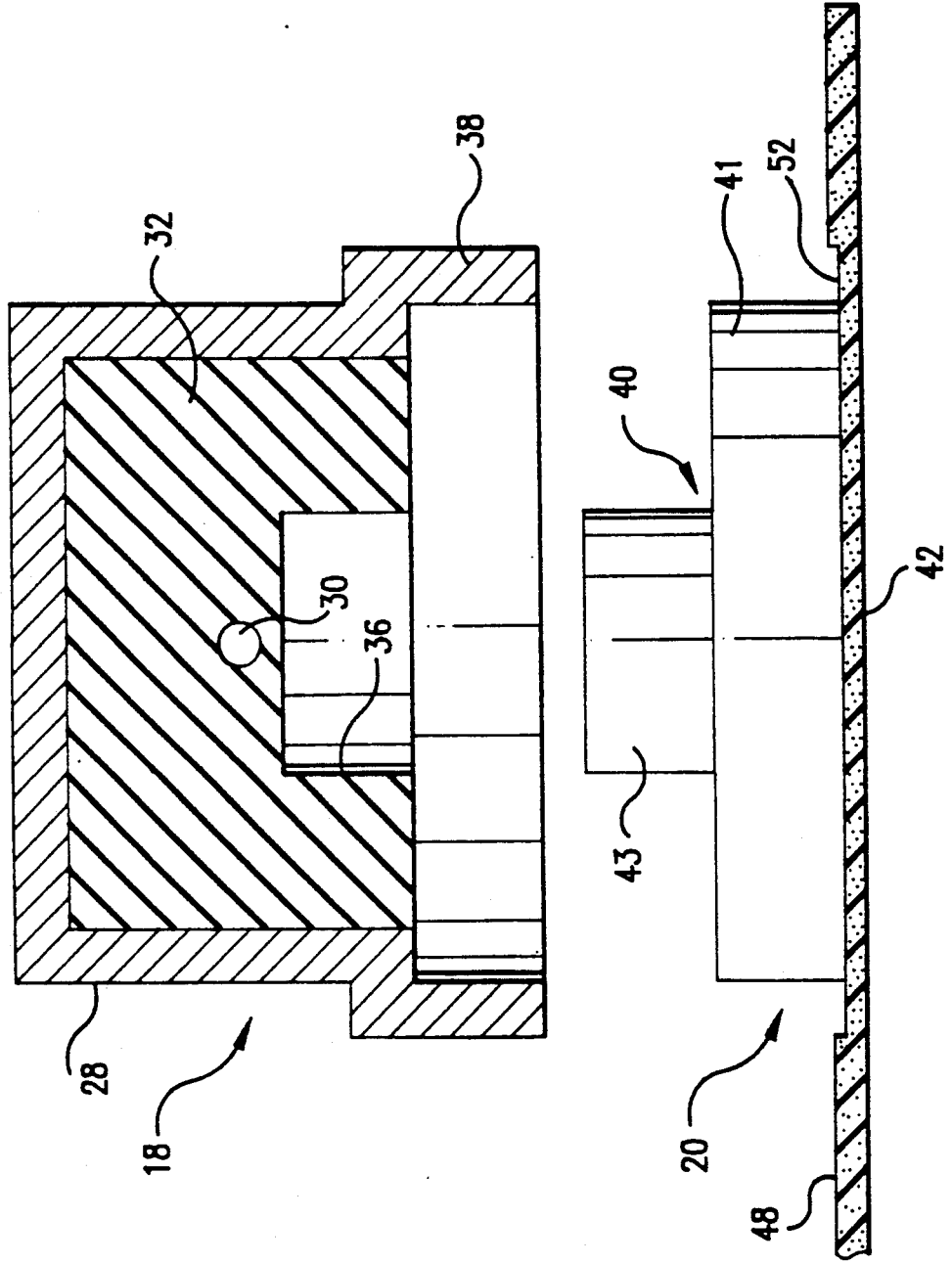
FIG. 3 is a sectional elevational view of the attachment element and the reusable antenna element.
Figure 5A:
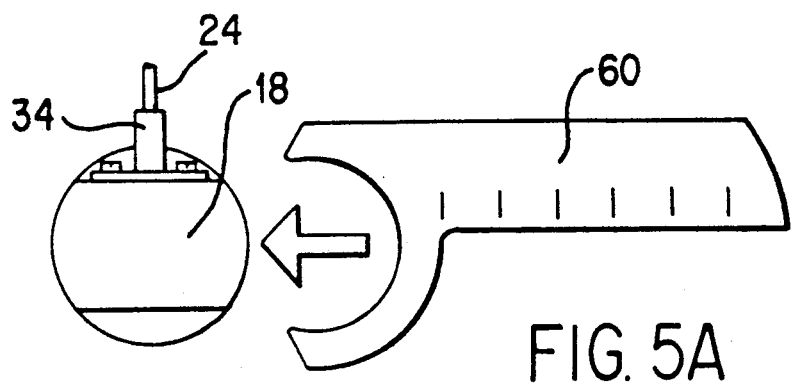
FIG. 5A is a plan view of the reusable antenna element and a detachable cannula guide.

Referring to FIG. 3, the antenna element 18 comprises an outer metallic housing 28, conveniently of aluminum, which is connected to the outer conductor of coaxial cable 24, an internal launching probe 30 connected to the center conductor of cable 24, and a mass of dielectric material 32 between the housing and probe effectively filling the interior of the housing. The cable 24 may be connected to antenna element 18 by a screw-on fitting 34 as shown in FIG. 5A.

Reverting to FIG. 3, it will be evident that the dielectric material 32 has a cylindrical recess 36 which, together with an enlarged diameter skirt portion 38 of the housing 28 defines a stepped female receiving formation which is complimentary to and interfits with a stepped dielectric button structure 40 on the disposable attachment element 20 having a larger diameter base portion 41 and a smaller diameter upper portion 43. Like dielectric materials are used in the antenna element 28 and for the button structure 40, and such materials have a high dielectric constant to match the impedance of the antenna to that of a patient's body. Thus, the dielectric constant preferably may be in a range K=9-80±. Examples of a suitable dielectric material are alumina, which has an intrinsically high dielectric constant, or alternatively a low loss tangent material (such as silicone rubber), such material being loaded with a material having a high dielectric constant, such as titanium dioxide. The dielectric material should also have a low dissipation constant, preferably less than 0.002.

With the attachment element adhered to a patient's skin, (as will be described) when the antenna element 18 is positioned on the button structure 40, the effect is to provide a complete microwave antenna assembly which is held in intimate contact with the patient's skin, a part of the antenna assembly being formed by the reusable antenna element 18 and another part of the antenna assembly being formed by the button structure 40 on the disposable attachment element 20.

The stepped configuration of the button structure is preferred to a simple cylinder structure, in that the stepped configuration maximizes reliability of detection of a disconnected or misconnected antenna, the stepped configuration being effectively the largest cylindrically symmetrical shape which can be removed from the reusable element. Using a plane cylindrical shape for the button may not provide a sufficiently effective signal change for reliable detection in case of misplacement of the antenna element. Typical dimensions of the button element 40 may, for example, be: diameter of base portion 0.720"±; height of base portion 0.10"; diameter of upper portion 0.184"±; and height of upper portion 0.15"±.

Figure 2:
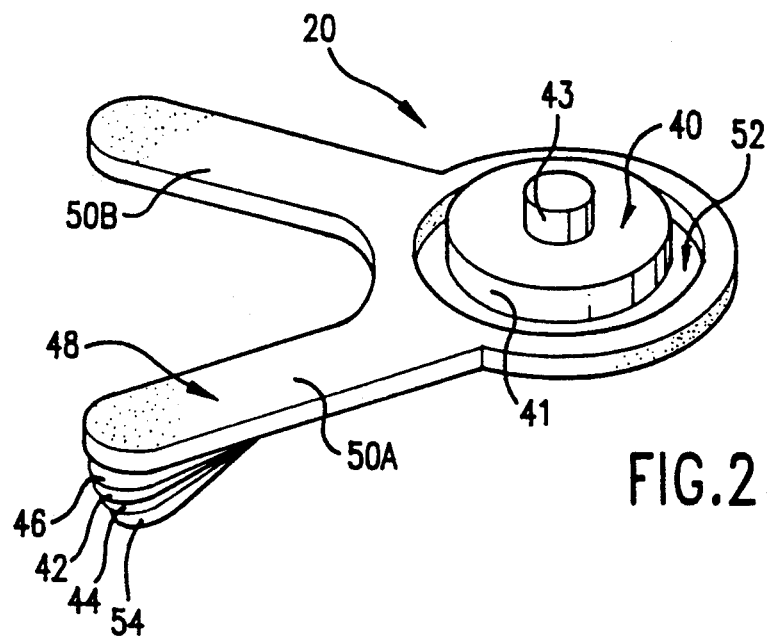
FIG. 2 is a perspective view of a disposable attachment element used in the apparatus for securing a reusable antenna element to a patient's skin.

As shown in FIG. 2, in a preferred embodiment of the invention, the button 40 is permanently adhered to a multilayer film 42. The film 42 has an adhesive layer 44 on its underside for contacting the patient's skin, such layer being a medical grade adhesive of moderate tack strength, so as not to irritate the skin on removal. The upper side of film 42 has an adhesive layer 46 of high tack strength, which bonds the film permanently both to the button 40 and also to a stabilizing layer 48 which is made of a conformal film such as polyethylene foam. The stabilizing layer, which may have a thickness of about 5 mils. helps to keep the antenna element oriented perpendicular to the skin surface and centered on the tip of cannula 14. The attachment element shown in FIG. 2 is of a generally circular shape with radiating arms 50A and 50B. The conformal film layer 48 has an annular cut-out portion defining a well 52 around the button and exposing an annular area of the adhesive layer 46 onto which the rim of the outer housing 28 of the antenna element fits, whereby in use, the antenna element is effectively held in intimate contact with the skin. For packaging purposes, the lower adhesive layer is provided with a peel-away release sheet 54, and a similar release sheet (not shown) may be provided for the exposed adhesive surface of well 52.

Figure 10A:
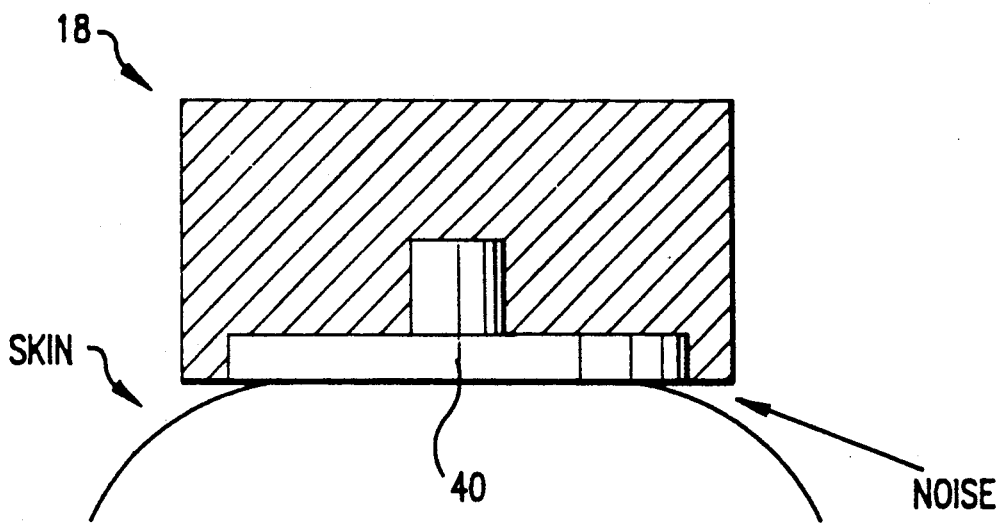
FIGS. 10A and 10B are diagrammatic sectional views of a microwave antenna on a patient's skin showing the improved effects obtainable by use of the invention.
Figure 10B:
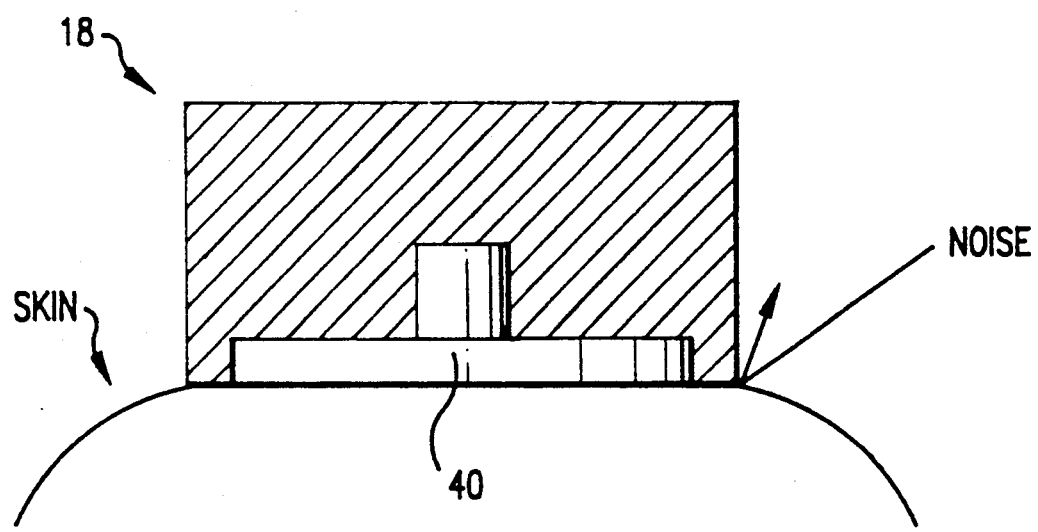

In use, the area of adhesive on well 52 holds the shielded undersurface of the antenna element intimately to the skin as shown diagrammatically in FIG. 10B and prevents extraneous environmental noise signals and the like degrading the transmission of microwave signal from the patient to the antenna, as may occur if the perimeter of the coupling were to be exposed, as in FIG. 10A thereby allowing the entry of stray radiation. In order to minimize environmental noise leakage into the antenna, the thickness of carrier film 42 and the adhesive layers 44, 46 should each be about 5 mils.

Figure 6:
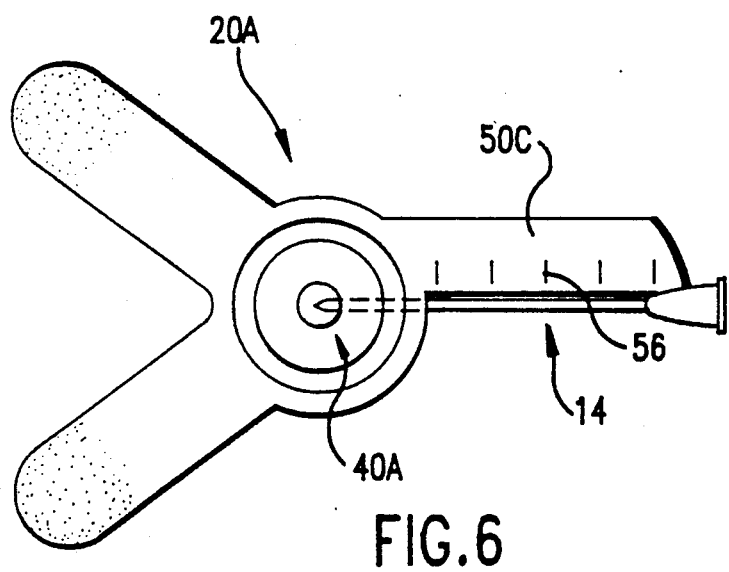
FIG. 6 is a plan view of still another form of attachment element showing its use in locating an antenna element relative to an infusion cannula.
Figure 7:
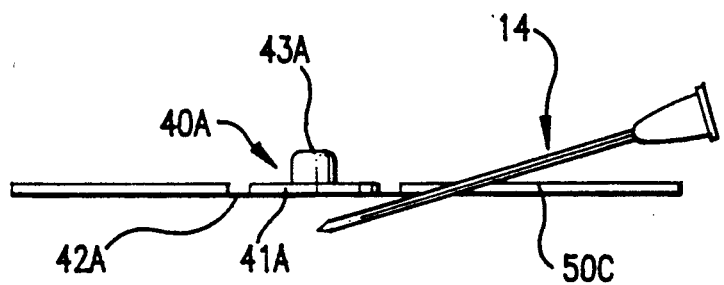
FIG. 7 is an elevational view of the attachment element and cannula shown in FIG. 6.

An alternative form of attachment element 20A is shown in FIGS. 6 and 7. Element 20A is structurally alike to the element 20 previously described except that it includes an additional radial arm 50C provided with a scale 56 which can be used to center the button 40 and thus the antenna element 18 accurately over the tip of an inserted cannula 14, by relating the scale length to the known overall cannula length.

Figure 8A:
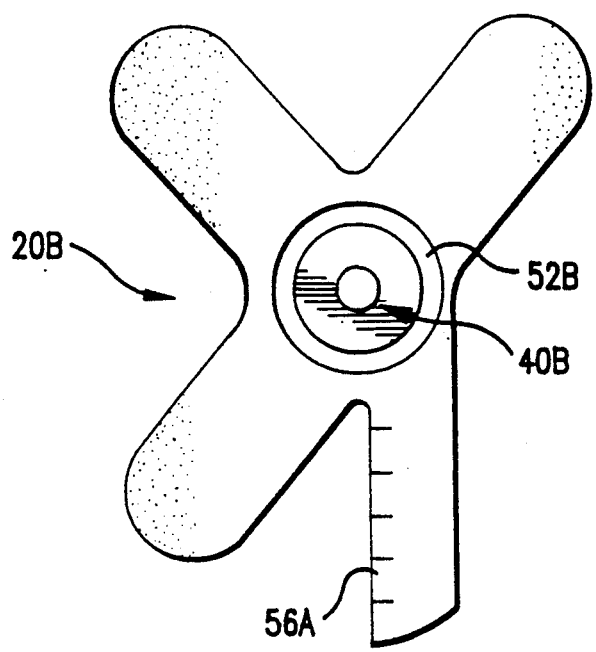
FIGS. 8A-8C are plan views of yet further forms of attachment elements.
Figures 8B, 8C:
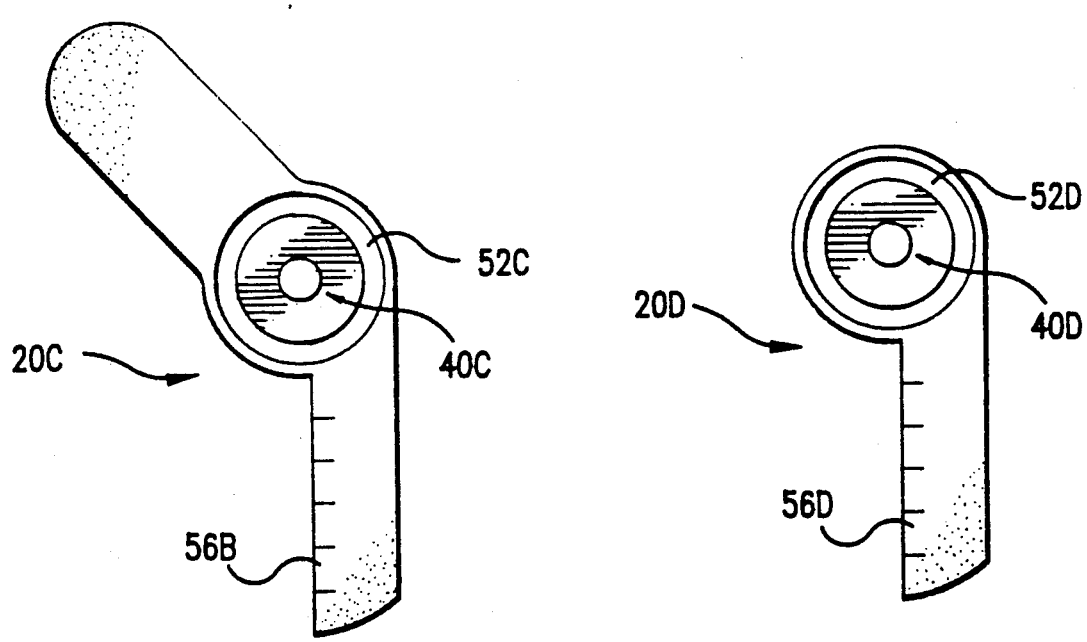

The weight of antenna element 18 and the force exerted by the stiffness of cable 24 between the antenna and the radiometer may tend to push the antenna away from its intended field of view. Accordingly, the attachment element 20, 20A should adhere sufficiently strongly to the skin to maintain the antenna placement, yet not irritate the skin when removed. This requires adequate adhesive surface area, provided inter alia by arms 50, to maintain a stable antenna position if the adhesive tack strength is to be low enough for patient comfort. In cases where loose skin is evident, as on some patients, an increased area of stabilizing film may be necessary to maintain the antenna position even though adhesion to the skin is greater than otherwise required. The requirement for greater adhesive surface area, however, is to be reconciled with the need for tactile and visual monitoring of the injection site before, during and after injection. Thus, a range of disposable attachment elements of different configurations may be provided to meet the needs of different patients. A number of such elements 20B, 20C and 20D are shown in FIGS. 8A, 8B and 8C which provide a range of greater stabilization (FIG. 8A) through greater open area for monitoring (FIG. 8C). Elements 20B-20D are each shown with an integral positioning guide 56A, 56B and 56C, but this may, in each case, be omitted to improve visibility of the injection site.

Figure 4:
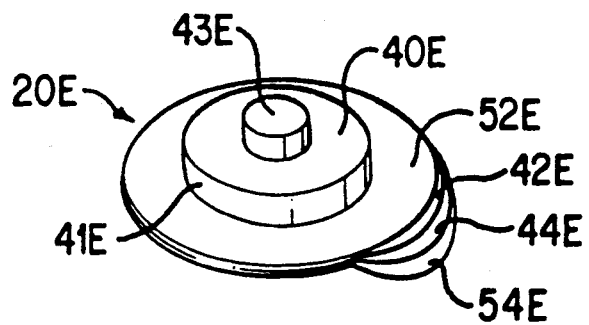
FIG. 4 is a perspective view of a modified form of attachment element.

A simplified form of attachment element 20E is shown in FIG. 4, in which the carrier film 42E does not extend beyond the periphery of the antenna element 18. An advantage of this embodiment is that it provides maximum tactile and visual monitoring of the injection site. While it is not essential for the carrier film and adhesive layers to extend beyond the button 40, adhesive film between the antenna housing 38 and the skin improves the antenna stability and shielding of noise from stray electromagnetic radiation as previously described.

Figure 5B:
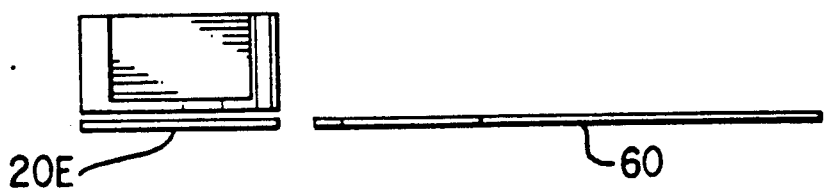
FIG. 5B is an elevational view of the antenna element and guide.

FIGS. 5A and 5B show a detachable guide 60 with scale 62 which can be positioned around button 40E, for example, to position element 20E relative to an inserted cannula as described previously. The detachable guide allows for improved accuracy in placement of the attachment element while maintaining maximum free monitoring area around the injection site.

A further embodiment of the invention, shown in FIG. 9, provides a sterile barrier or envelope 70 of suitable synthetic film, for the antenna element 18, and includes a cut-out 72 for exposing the rim of antenna housing 38 and an adhesive ring 74, around the cut-out for adhering the envelope to the attachment element 20. The envelope prevents contamination of the reusable antenna element.

The various attachment elements described above are relatively inexpensive to manufacture and are intended for disposable once off usage with the reusable parts of the system. While only preferred embodiments of the invention have been described in detail, the invention is not limited thereby and modifications can be made within the scope of the attached claims.

We claim:

1. A system for microwave detection of extravasation of liquid from a blood vessel of a patient into which the liquid is injected, the system including microwave antenna means for receiving microwave emission signals from the patient and processing means connected with the antenna means for responding to changes in said signals representative of extravasation, the antenna means including a reusable antenna element connected to said processing means, a disposable attachment element for adhering to a patient's skin over an injection site, and interfitting male and female coupling means on the attachment element and the antenna element respectively for releasably securing the antenna element on the attachment element in intimate contact with the patient's skin.

2. A system for microwave detection of extravasation of liquid from a blood vessel of a patient into which the liquid is injected, the system including microwave antenna means for receiving microwave emission signals from the patient and processing means connected with the antenna means for responding to changes in said signals representative of extravasation, the antenna means including a reusable antenna element connected to said processing means, a disposable attachment element for adhering to a patient's skin over an injection site, and interfitting male and female coupling means on the attachment element and the antenna element respectively for releasably securing the antenna element on the attachment element in intimate contact with the patient's skin, wherein the reusable antenna element comprises a conductive outer housing, a conductive launching probe within said housing and a dielectric material within said housing separating the launching probe from the housing, further wherein said female element comprises a recess in the dielectric material and the male element comprises a button of like dielectric material on the attachment element to fit in said recess.

3. The system defined in claim 2, wherein the button comprises a cylindrical larger diameter base portion and a cylindrical smaller diameter upper portion, the upper portion adapted to fit in said recess and the housing of the antenna element having an enlarged skirt portion to receive said base portion of the button.

4. The system defined in claim 2, further including an elongate scale member removably attachable to said button for centering the button relative to a tip of an injection cannula used for injecting liquid into the patient's blood vessel.

5. The system defined in claim 2, wherein the attachment element comprises a flexible carrier film having an adhesive undersurface, the button being located on an upper surface of said carrier film.

6. The system defined in claim 5, wherein the carrier film has a portion surrounding the button with an adhesive upper surface to secure the housing of the antenna element.

7. The system defined in claim 6, further including a sterile envelope enclosing the antenna element with a circular cut-out accommodating a rim portion of said housing and a ring of adhesive around said cut-out.

8. The system defined in claim 6, wherein the carrier film has an extended portion beyond said surrounding portion and the extended portion is covered by a conformal flexible stabilizing layer.

9. The system defined in claim 8, wherein the extended portion has a circular section with at least one radial leg extending outwardly from said circular section.

10. The system defined in claim 9, wherein the leg is provided with a longitudinal scale for centering the button relative to a tip of an injection cannula used for injecting the liquid into the patient's blood vessel.

11. A system for microwave detection of extravasation of liquid from a blood vessel of a patient into which the liquid is injected, the system including microwave antenna means for receiving microwave emission signals form the patient and processing means connected with the antenna means for responding to changes in said signals representative of extravasation, the antenna means including a reusable antenna element connected to said processing means, a disposable attachment element for adhering to a patient's skin over an injection site, and interfitting male and female coupling means on the attachment element and the antenna element respectively for releasably securing the antenna element on the attachment element in intimate contact with the patient's skin, wherein the processing means includes a radiometer connected to the antenna element by a coaxial cable having an inner conductor connected to the launching probe and an outer conductor connected to the housing.

12. The system defined in claim 11, wherein the processing means further includes an injector head for operating a syringe to inject the liquid, and microprocessor means associated with the injector head and operated by signals received from the radiometer to terminate injection responsive to changes in said signals representative of extravasation.

13. A reusable microwave antenna element for receiving microwave radiation from a body of a patient during injection of liquid into a blood vessel, by attachment of the antenna element in intimate contact with skin of the patient, comprising an outer cup-like conductive housing with a rim for securing in intimate contact with the skin, a conductive launching probe leading into said housing, a dielectric material filling the housing and separating the launching probe from the housing, and a recess in the dielectric material for receiving part of a button of like dielectric material on an attachment element used for securing the antenna element to the patient's skin.

14. An antenna element as claimed in claim 13, wherein the housing has an enlarged skirt portion under the dielectric material to receive a base portion of a dielectric button which has a smaller upper portion adapted to fit in said recess.

15. A disposable attachment element for securing a microwave antenna element to skin of a patient to receive microwave radiation from the patient during injection of liquid into a blood vessel, the element comprising a flexible carrier sheet having an adhesive undersurface, a button of dielectric material on an upper surface of the sheet, and the sheet having an adhesive upper surface portion surrounding the button to receive a peripheral portion of a microwave antenna element coupled to the attachment element with the button received in a corresponding recess of the antenna element.

16. An attachment element as claimed in claim 15, further including an elongate measuring scale element releasably attachable to the button for locating the button on a patient's skin relative to the tip of an injection cannula inserted into a blood vessel.

17. A disposable attachment element for securing a microwave antenna element to skin of a patient to receive microwave radiation from the patient during injection of liquid int a blood vessel, the element comprising a flexible carrier sheet having an adhesive undersurface, a button of dielectric material on an upper surface of the sheet, and the sheet having an adhesive upper surface portion surrounding the button to receive a peripheral portion of a microwave antenna element coupled to the attachment element with the button receive in a corresponding recess of the antenna element, wherein the button has a stepped configuration with a larger base portion and smaller upper portion.

18. An attachment element as claimed in claim 17, wherein the carrier element includes an extension portion surrounding said upper surface portion with a flexible conformal covering layer over said extension portion.

19. An attachment element as claimed in claim 18, wherein the extension portion has a circular configuration with at least one radially outwardly extending leg.

20. An attachment as claimed in claim 19, wherein said leg is provided with a lengthwise measuring scale for locating the button on a patient's skin relative to the tip of an injection cannula inserted into a blood vessel.

21. A method of monitoring electromagnetic microwave emission from a patient during injection of liquid into a blood vessel to detect extravasation of the liquid comprising providing an electromagnetic microwave detection system including microwave antenna means having a reusable microwave antenna element connected with processing means for responding to changes of microwave emission from the patient representative of extravasation, and a disposable attachment element for securing the antenna element to the patient's skin by means of male and female coupling elements on the attachment element and the antenna element respectively, adhesively securing the attachment element to the patient's skin over an injection site, coupling the antenna element to the attachment element to form the antenna means, using the antenna means to monitor for extravasation during injection of the liquid, uncoupling the antenna element from the attachment element after injection for reuse of the antenna element, and removing the attachment element from the patient's skin for disposal.

22. A method of monitoring electromagnetic microwave emission from a patient during injection of liquid into a blood vessel to detect extravasation of the liquid comprising providing an electromagnetic microwave detection system including microwave antenna means having a reusable microwave antenna element connected with processing means for responding to changes of microwave emission from the patient representative of extravasation, and a disposable attachment element for securing the antenna element to the patient's skin by means of male and female coupling elements on the attachment element and the antenna element respectively, adhesively securing the attachment element to the patient's skin over an injection site, coupling the antenna element to the attachment element to form the antenna means, using the antenna means to monitor for extravasation during injection of the liquid, uncoupling the antenna element form the attachment element after injection for reuse of the antenna element, and removing the attachment element from the patient's skin for disposal, further including the steps of providing the attachment element with a linear measuring scale prior to securing the attachment element to the patient's skin, and using the measuring scale to relate the position of the attachment element relative to a cannula inserted into the blood vessel for performing the liquid injection.

* * * * *